(12) United States Patent
Kucharczyk et al.

(10) Patent No.: US 6,537,232 B1
(45) Date of Patent: Mar. 25, 2003

(54) INTRACRANIAL PRESSURE MONITORING DEVICE AND METHOD FOR USE IN MR-GUIDED DRUG DELIVERY

(75) Inventors: John Kucharczyk, Minneapolis, MN (US); Charles L. Truwit, Wayzata, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/541,288

(22) Filed: Apr. 3, 2000

Related U.S. Application Data (63) Continuation-in-part of application No. 08/856,894, filed on May 15, 1997, now Pat. No. 6,061,587.

(51) Int. Cl.⁷ ............................................... A61B 5/05
(52) U.S. Cl. ...................... 600/561; 600/411
(58) Field of Search .................. 600/411, 420, 600/423, 561, 433; 604/48, 65, 66, 503, 505, 506, 507, 508, 510

(56) References Cited

U.S. PATENT DOCUMENTS

| | | | |
|---|---|---|---|
| 4,014,319 A | 3/1977 | Favre ............................. | 128/2 |
| 4,026,276 A | 5/1977 | Chubbuck ....................... | 128/2 |
| 4,062,354 A | 12/1977 | Taylor et al. ................... | 128/2 |
| 4,080,653 A | 3/1978 | Barnes et al. ................. | 364/417 |
| 4,114,603 A | 9/1978 | Wilkinson ....................... | 128/2 |
| 4,114,606 A | 9/1978 | Seylar ........................... | 128/2.05 |
| 4,147,161 A | 4/1979 | Ikebe et al. ..................... | 128/2 |
| 4,156,422 A | 5/1979 | Hildebrandt et al. ........ | 128/748 |
| 4,173,228 A | 11/1979 | Van Steenwyk et al. .... | 128/653 |
| 4,210,029 A | 7/1980 | Porter ......................... | 73/705 |
| 4,265,252 A | 5/1981 | Chubbuck et al. .......... | 128/748 |
| 4,343,038 A | 8/1982 | Enz .............................. | 365/36 |
| 4,385,636 A | 5/1983 | Cosman ....................... | 128/748 |
| 4,438,773 A | 3/1984 | Letterio ....................... | 128/748 |
| 4,465,075 A | 8/1984 | Swartz ......................... | 128/672 |
| 4,471,786 A | 9/1984 | Inagaki et al. ............... | 128/748 |
| 4,600,013 A | 7/1986 | Landy et al. ................. | 128/748 |
| 4,621,647 A | 11/1986 | Loveland ..................... | 128/748 |
| 4,627,443 A | 12/1986 | Chubbuck et al. ........... | 128/748 |
| 4,677,985 A | 7/1987 | Bro et al. ..................... | 128/691 |
| 4,703,757 A | 11/1987 | Cohen .......................... | 128/667 |
| 4,711,246 A | 12/1987 | Alderson ..................... | 128/667 |

(List continued on next page.)

OTHER PUBLICATIONS

Cox, R.W., et al., "Real–Time Functional Magnetic Resonance Imaging", *Magnetic Resonance in Medicine, 33*(2), 230–236 (1995).

Ortler, M., et al., "Transcutaneous Pressure–adjustable Valves and Magnetic Resonance Imaging: An ex vivo Examination of the Codman–Medos Programmable Valve and the Sophy Adjustable Pressure Valve.", *Neurosurgery, 40*(5), 1050–1057 (1997).

*Primary Examiner*—Francis J. Jaworski
*Assistant Examiner*—Runa Shah Qaderi
(74) *Attorney, Agent, or Firm*—Mark A. Litman & Assoc. P.A.

(57) ABSTRACT

A device and method for monitoring intracranial pressure during magnetic resonance (MR) image-guided neurosurgical procedures, such as intracranial drug delivery procedures, wherein an MR-compatible microsensor pressure transducer coupled to a pressure sensing diaphragm located a) at the tip, b) on a lateral side, and/or c) in multiple locations of an MR-compatible catheter is inserted into a lateral cerebral ventricle, cerebral cistern, subarachnoid space, subdural or extradural spaces, venous sinuses, or intraparenchymal tissue locations under MR imaging guidance, and is used to record intracranial pressures over hours to days in patients undergoing diagnostic or therapeutic neurologic interventions.

3 Claims, 2 Drawing Sheets

U.S. PATENT DOCUMENTS

| | | | |
|---|---|---|---|
| 4,723,556 A | 2/1988 | Sussman | 128/748 |
| 4,738,267 A | 4/1988 | Lazorthes et al. | 128/748 |
| 4,772,257 A | 9/1988 | Hakim et al. | 604/9 |
| 4,805,634 A | 2/1989 | Ullrich et al. | 128/748 |
| 4,841,986 A | 6/1989 | Marchbanks | 128/746 |
| 4,846,191 A * | 7/1989 | Brockway et al. | |
| 4,858,619 A | 8/1989 | Toth | 128/748 |
| 4,885,002 A | 12/1989 | Watanabe et al. | 604/9 |
| 4,903,707 A | 2/1990 | Knute et al. | 128/748 |
| 4,995,401 A | 2/1991 | Bunegin et al. | 128/748 |
| 5,000,049 A | 3/1991 | Cooper et al. | 73/730 |
| 5,005,584 A | 4/1991 | Little | 128/748 |
| 5,042,486 A | 8/1991 | Pfeiler et al. | 128/653 |
| 5,074,310 A | 12/1991 | Mick | 128/748 |
| 5,108,364 A | 4/1992 | Takezawa et al. | 604/43 |
| 5,113,868 A | 5/1992 | Wise et al. | 128/675 |
| 5,117,835 A | 6/1992 | Mick | 128/748 |
| 5,191,898 A | 3/1993 | Millar | 128/748 |
| 5,211,165 A | 5/1993 | Dumoulin et al. | 128/653.1 |
| 5,230,338 A | 7/1993 | Allen et al. | 128/653 |
| 5,255,680 A | 10/1993 | Darrow et al. | 128/653.1 |
| 5,307,808 A | 5/1994 | Dumoulin et al. | 128/653.2 |
| 5,318,025 A | 6/1994 | Dumoulin et al. | 128/653.2 |
| 5,325,865 A | 7/1994 | Beckman et al. | 128/748 |
| 5,383,454 A | 1/1995 | Bucholz | 128/653.1 |
| 5,410,287 A | 4/1995 | Laskaris et al. | 335/216 |
| 5,519,372 A | 5/1996 | Palkovich et al. | 335/216 |
| 5,565,831 A | 10/1996 | Dorri et al. | 335/216 |
| 5,713,357 A | 2/1998 | Meulenbrugge et al. | 128/653.2 |
| 5,715,822 A | 2/1998 | Watkins et al. | 128/653.5 |
| 5,964,705 A * | 10/1999 | Truwit et al. | |
| 5,984,705 A | 11/1999 | Miyazaki et al. | 439/304 |
| 6,033,366 A * | 3/2000 | Brockway et al. | |
| 6,061,587 A * | 5/2000 | Kucharczyk et al. | |
| 6,201,980 B1 * | 3/2001 | Darrow et al. | |
| 6,233,474 B1 * | 5/2001 | Lemelson | |
| 6,248,080 B1 * | 6/2001 | Miesel et al. | |

\* cited by examiner

Fig. 3

INTRACRANIAL PRESSURE MONITORING DEVICE AND METHOD FOR USE IN MR-GUIDED DRUG DELIVERY

RELATED APPLICATIONS

This application is a continuation-in-part application of U.S. patent application Ser. No. 08/856,894, now U.S. Pat. No. 6,061,587.

BACKGROUND OF THE INVENTION

1. Field of the Invention

This invention relates to the design, construction, and use of a device for acute and chronic measurement of intracranial pressures in the human central nervous system, particularly during magnetic resonance (MR) imaging procedures, in particular during the injection or infusion of therapeutic drugs into the brain parenchyma. The present invention is an improvement over conventional methods and apparatus for measuring intracranial pressure, such as ventriculostomy with an external transducer, epidural strain gauge transducer, pressure sensitive epidural capsule, pressure sensitive subdural capsule, or subarachnoid pressure transducer.

2. Background of the Prior Art

Elevated intracranial pressure (ICP) can result from a variety of pathophysiological disturbances and frequently presents a major problem in the management of patients with head injury or other neurological disorders and diseases, including brain tumors and intracerebral hemorrhage. Although numerous autoregulatory and compensatory mechanisms protect the brain against elevations in ICP, if the ICP is increased to levels approximately equal to or greater than those of the arterial blood pressure, cerebral blood flow can be severely compromised leading to brain herniation and death.

The primary aim of ICP monitoring is to provide an early warning of a deteriorating condition so as to enable corrective therapy to be implemented. The accuracy required when measuring ICP is typically of the order of 1–2 mm Hg, but equally important is the reliability of the data. To ensure reliability, the calibration of any measuring device must be easily checked and adjusted as necessary. In addition to the steady-state accuracy of any sensing device and recording system, it is essential to have adequate dynamic response characteristics in the measuring device.

It is also essential that measurements can be made with minimum interference to the patient. To satisfy this objective, non-invasive methods of determining changes in ICP indirectly have been attempted using, for example, impedance plethysmography. Such non-invasive methods have been used successfully in neonates. However, in adults, methods which give the most accurate measurements require access into the cranial cavity and are therefore more invasive.

Invasive ICP devices have generally evolved in two basic directions. The first is based on implanting a sensor within the cranium. The second is based on mounting the sensor externally and connecting the measurement site through a fluid-filled transmission line. The three main sites for ICP Ring are the lateral ventricle, the extradural space, and the subdural or subarchmoid spaces.

U.S. Pat. No. 4,014,319 to Favre discloses an intracranial pressure transducer comprising a small sealed capsule positioned in a trephined hole in the patient's skull, wherein a sensor diaphragm in contact with the dura mater is displaced by changes in intracranial pressure and produces an output signal proportional to the change in intracranial pressure. U.S. Pat. No. 4,026,276 to Chubbuck discloses a pressure monitoring apparatus implantable in the cranium, wherein the apparatus comprises a passive resonant circuit with inductance and capacitance capability for measuring intracranial pressure by comparison to a reference ambient pressure.

U.S. Pat. No. 4,062,354 to Taylor et al. discloses an intracranial pressure transducer system comprising a holding bracket containing sensor elements which is positioned against the dura of the brain, wherein the elements within the holding bracket transmit electromagnetic signals related to the intracranial pressure to a receiver outside the patients body.

U.S. Pat. No. 4,080,653 to Barnes et al. discloses a method and apparatus for recording intracranial pressure utilizing a transducer amplifier.

U.S. Pat. No. 4,114,603 discloses an intracranial pressure monitoring device comprising a pressure-sensitive catheter insertable between the dura mater and arachnoid membrane. U.S. Pat. No. 4,114,606 discloses a monitoring apparatus for intracranial pressure measurement, wherein electromagnetic radiation is imposed on a passive circuit implanted in the cranium, the frequency at which the radiation is absorbed reflecting intracranial pressure.

U.S. Pat. No. 4,147,161 to Ikebe et al. discloses a system for measuring or monitoring intracranial pressure which comprises a non-elastic detecting pouch inserted between the skull and the brain, wherein a pressure measuring device in the liquid in the pouch indirectly measures the intracranial pressure.

U.S. Pat. No. 4,156,422 to Hildebrandt discloses an apparatus for treating hydrocephalus comprising housing which contains subcutaneously implantable components for measuring and controlling fluid pressure, wherein a second housing outside the patient contains measuring and control components whereby an intracerebral space may be automatically drained in response to a predetermined adjustable ICP.

U.S. Pat. No. 4,210,029 to Porter discloses a differential sensor unit utilizing fiber optic light guides, wherein three light guides pass within a pneumatic line into one end of a rigid cylindrical envelope implanted in the skull. Detectors are arranged to actuate pressure display and pneumatic controls to adjust the internal pressure of the envelope to match the ICP and thereby measure the ICP. U.S. Pat. No. 4,265,252 to Chubbuck discloses an implantable transsensor device containing a passive RF resonant circuit which is responsive to changes in ICP.

U.S. Pat. No. 4,385,636 to Cosman discloses an implantable telemetric differential pressure sensing device comprising a planar closed conductive loop which moves with a flexible diaphragm, wherein the resonant frequency of the conductive loop is detected telemetrically to determine pressure in a body compartment.

U.S. Pat. No. 4,343,038 to McKean discloses a magnetic field generator and magnetic pick-up coil contained in an implanted ICP monitoring device. U.S. Pat. No. 4,354,506 to Sakaguchi et al discloses an intracranial pressure gauge which comprises a powerless resonance circuit composed of a coil and a condenser, a sensor equipped with an implantable pressure-sensitive section capable of changing the inductance or the capacitance of the condenser in response to a change in ICP. U.S. Pat. No. 4,438,773 to Letterio discloses an implantable subarachnoid bolt for use in measuring ICP. U.S. Pat. No. 4,465,075 to Swartz discloses an integrated circuit including a pressure transducer and temperature compensation circuit.

U.S. Pat. No. 4,471,786 to Inagaki discloses a telemetering intracranial pressure transducer for detecting ICP, wherein a pressure-receiving layer disposed in contact with the dura mater transmits an output signal to an telemetering transmission circuit housed entirely beneath the patients scalp.

U.S. Pat. No. 4,600,013 to Landy et al. discloses a probe for ICP measurements in the subarachnoid space, said probe comprising a threaded shaft having a lumen in contact with a pressure transducer.

U.S. Pat. No. 4,621,647 to Loveland discloses an apparatus for monitoring and regulating ICP, wherein a manometer, transducer and regulator are interconnected by tubing and stopcocks. U.S. Pat. No. 4,627,443 to Chubbuck discloses an X-ray readable implantable pressure sensor,, wherein shifting of the radiopaque means is observed to indicate the change in pressure of a body cavity.

U.S. Pat. No. 4,677,985 to Bro et al. discloses an intracranial probe to monitor both ICP and blood flow by thermal diffusion and hydrogen clearance techniques.

U.S. Pat. No. 4,703,757 to Cohen discloses an optical fiber pressure transducer, wherein variations in transversely applied pressure to an elongated flexible fiber results in proportional light refraction and corresponding output signal.

U.S. Pat. No. 4,711,246 to Alderson discloses a miniaturized pressure transducer, wherein light transmitted through a single optical fiber is reflected by a diaphragm in accordance with the pressure being measured.

U.S. Pat. No. 4,723,556 to Sussman discloses an intracranial ventricular catheter assembly, wherein a pressure sensing device is connected to the proximal catheter. U.S. Pat. No. 4,738,267 to Lazorthes discloses an implantable intracranial pressure sensor, wherein a pressure-sensitive diaphragm placed directly on the dura mater transmits the intracranial pressure through a resistive type transducer. U.S. Pat. No. 4,772,257 to Hakim et al. discloses an external programmer for magnetically-adjustable cerebrospinal fluid shunt valve.

U.S. Pat. No. 4,858,619 to Toth discloses an intracranial pressure monitoring system, wherein relief valves are combined with a pressure sensor for automatic venting of cerebrospinal fluid during elevated ICP.

U.S. Pat. No. 4,805,634 to Ullrich discloses an adapter assembly for accurately positioning a removable biosensor implanted in the cranium.

U.S. Pat. No. 4,841,986 to Marchbanks discloses a method and apparatus for measuring ICP, wherein a pressure sensor placed against the eardrum indirectly detects ICP changes based on displacement of the eardrum.

U.S. Pat. No. 4,903,707 to Knute et al. discloses a ventricular catheter assembly comprising a catheter and a bolt, wherein the catheter can be inserted to a predetermined depth into the cranium. U.S. Pat. No. 4,995,401 to Bunegin et al. discloses a device for measuring anterior fontanelle pressure, wherein ICP changes can be detected noninvasively.

U.S. Pat. No. 5,000,049 to Cooper et al. discloses an apparatus for measuring fluid pressures using a catheter device.

U.S. Pat. No. 5,005,584 to Little discloses a fiber optic transducer utilizing a flexible membrane to transduce pressure by interrupting light transmission between fiber optic paths in a catheter or guide wire carrier.

U.S. Pat. Nos. 5,074,310 and 5,117,835 to Mick disclose a method and apparatus for in non-invasively measuring changes in ICP, wherein a predetermined vibration signal is applied to one location in the skull and an output vibration signal is detected from another location in the skull reflecting ICP changes over time.

U.S. Pat. No. 5,108,364 to Takezawa et al. discloses a monitoring catheter for medical use comprised of multiple tubes equipped for fluid delivery and removal, pressure measurement, and temperature measurement. U.S. Pat. No. 5,113,868 to Wise at al. discloses a pressure sensing catheter system comprising a catheter, a pressure sensor, and a signal conduit means within the catheter for signals between an external monitor and the pressure sensor, the signal conduit including two electrical conductors which are connectable to the external monitor.

U.S. Pat. No. 5,191,898 to Millar discloses a cerebroventricular catheter means of measuring ICP and injecting or withdrawing cerebrospinal fluid, wherein a transducer positioned at the end of the cerebroventricular catheter and electrically coupled to a monitor allows for ICP monitoring.

U.S. Pat. No. 5,292,899 to Watanabe et al. discloses a method for measuring ICP by using a device comprising a reservoir implantable under the skin of a patient and into which reservoir cerebrospinal fluid can be introduced from the ventricle of the patient, a flexible dome configured to be upwardly projected from said reservoir by the pressure of the cerebrospinal fluid and flexibly deformable according to an external force, a pressing part for pressing against said dome through the skin, a pressing-part-driving means for driving said pressing part pressing the dome and a flexible membrane provided at the tip of the pressing part and having an interior filled with a fluid, the method comprising: pressing the flexible membrane of the pressing part against the dome of the reservoir through the skin by means of the pressing-part-driving means after a zero point correction of the pressure transducer is performed by communicating the interior of the flexible membrane with the atmosphere.

U.S. Pat. No. 5,325,865 to Beckman et al. discloses a catheter assembly for measuring fluid pressure in a body cavity, comprising an optical converter responsive to an electrical power source for energizing a light-emitting diode which has drift characteristics which vary in response to temperature, and a detection circuit. U.S. Pat. No. 5,230,338 to Allen et al. discloses an interactive image-guided system for displaying images corresponding to the placement of a surgical probe in the body. U.S. Pat. No. 4,173,228 to Van Steenwyk et al, and U.S. Pat. No. 5,042,486 to Pfeiler et al. disclose medical probes wherein electromagnetic signals are propagated between one antenna on the tip of the probe inserted into a body region and several antennae outside the body. The position and orientation of the probe tip are determined from the signals transmitted between said antennae.

U.S. Pat. No. 5,211,165 to Dumoulin et al., U.S. Pat. No. 5,255,680 to Darrow and Dumoulin, U.S. Pat. No. 5,307,808 to Dumoulin et al., and U.S. Pat. No. 5,318,025 to Dumoulin et al. additionally disclose a tracking system in which radiofrequency signals emitted by an invasive device, such as a catheter, are detected and used to measure the device's position and orientation in a patient. Localization of devices in situ is achieved by transmit radiofrequency coils positioned at its distal end, which are detected by receive radiofrequency coils positioned around the imaging volume of interest. The position of the device, as determined by the tracking system, is superimposed upon independently acquired diagnostic images. U.S. Pat. No. 5,383,454 to Bucholz discloses a system for indicating a position of a tip of a probe which is positioned within an object on images of the object, wherein a computer employing translational software translate the position of the tip of said probe into a coordinate system corresponding to the coordinate system of the cross-sectional images.

Each of the above cited patents provide advantages and disadvantages for ICP monitoring. For instance, intraventricular catheters are accurate but may be difficult to position in the presence of brain swelling and shifting of tissue. Subarachnoid devices are easily placed, but may underestimate higher ICP pressures, particularly if they are not coplanar to the brain surface. Epidural devices require placement through a burr hole and can be hampered by recording artifacts, dampening, and problems with calibration.

Moreover, none of the above cited patents disclose a method or apparatus for evaluating changes in ICP resulting from the direct injection or infusion of drug agents into brain tissues. One of the significant problems with direct drug delivery to living tissue is assuring that the drug is accurately distributed to target receptor locations. The efficacious delivery of therapeutic agents for the treatment of brain tumors or neurodegenerative diseases, as two examples, requires that the agents be delivered as close to their receptors in the brain as possible, while minimizing increases in intracranial pressure during and after drug delivery. Liquid drug agents delivered into the brain through implanted catheters will disperse from the site of injection at variable rates depending on a number of factors, including the physicochemical characteristics of the drug, capillary uptake, metabolic degradation and excretion of the drug, size of the extracellular space (the volume fraction), and geometry of the brain cell microenvironment (tortuosity). The degree to which each of these factors influences the distribution of a particular drug agent may be an important determinant of the effectiveness of drug treatment of diseases of the central nervous system.

Ideally, drug material injected into the brain infiltrates the extracellular space, and the subsequent tissue distribution of the drug is governed mainly by its molecular weight, molecular radius, and the tissue matrix structure into which the material has been injected. However, injection of a solution containing a macromolecular drug agent into the intraparenchymal extracellular space of the brain may instead result in the injected drug being sequestered as a cavity or depot. If the injected drug solution forms a fluid-filled cavity in the tissue, this may lead to tissue selling, an increase in ICP and, secondarily, altered interstitial transport of the drug solute.

It is therefore apparent that increases in ICP induced by intraparenchymal injections of liquid drug agents can injure tissues directly, or indirectly by retarding the efficacious distribution of the drug due to tissue swelling and retarded interstitial solute transport. Thus, it is important to be able to monitor any local and regional increases in ICP resulting from injections of liquid drug agents directly into the brain parenchyma. The availability of an MR-visible drug delivery device which incorporates a method means for monitoring local and regional changes in ICP would make it possible to obtain near real-time information on tissue pressure changes during interventional procedures in an intra-operative MR system.

SUMMARY OF THE INVENTION

The present invention discloses a device and method for monitoring intracranial pressure (ICP) during MR image-guided neurosurgical procedures, wherein an MR-compatible microsensor pressure transducer coupled to a pressure sensing diaphragm is positioned or located on the surface of an interventional device, such as at or near either a) a distal tip of the device and b) lateral surfaces of an MR-compatible device such as an MR-compatible multilumen drug delivery catheter. One or preferably more than one sensing element may be present on the interventional device. The microsensor and diaphragm detect and monitor local and regional changes in ICP during and after delivery (especially immediately after delivery while changes in local concentration of the injectant or drug agents can be observed) of liquid drug agents into the brain parenchyma. In at least one method within the scope of the invention, the pressure sensor includes a pressure transducer for converting a sensed pressure into a first electrical signal which is detectable by an external monitor transmission after transmission over a signal conduit means. There may be a first switching device for selectively controlling when the first electrical signal is generated, and a device that is responsive to at least one command signal from the external monitor for controlling the delivery of drug solution in response to detected alterations in ICP. In a practice of the present invention, the ICP monitoring device may also be inserted into any convenient location such as a lateral cerebral ventricle, cerebral cistern, subarachnoid space, subdural or extradural space, or venous sinus, under MR imaging guidance, and used to record intracranial pressures over seconds, minutes, hours to days in patients undergoing diagnostic or therapeutic neurologic interventions. Continuous monitoring of the ICP in real time may also be effected in this invention.

The invention also relates to an apparatus for the determination or monitoring of intracranial pressure comprising:

an article that is insertable into the tissue or vasculature of the brain, said article comprising a pressure sensing element, a signal transmitting connector connecting the pressure sensing element and a signal reader (meaning artificial intelligence or artificial memory such as a reader, recorder or analyzer), the signal reader being able to (read, record, or analyze) signals from said pressure sensing element to indicate hydrostatic pressure or changes in hydrostatic pressure. The pressure sensing element may, for example, comprise a solid state pressure sensing element, a curved semiconductor element, or a physical sensor, alone or combined with electronic or electrical elements, such as a diaphragm (e.g., a diaphram or flexible, compressible, deflatable, inflatable or pressure moveable layer or element that has one surface that is exposed to an environment in which the pressure sensing element is placed, such as within the fluid or tissue fluid of a patient), as where a second surface of the diaphragm defines part of an internal cavity within the pressure sensing element, and movement of said diaphragm causes changes in pressure within the internal cavity. A pressure reading device may then be present within said internal cavity and the pressure sensing element is attached to the connector by electrical attachment of the pressure reading device to the connector. The pressure-sensing device may be connected to or independent of a device for the delivery of chemical agents into the bodily fluid, and particularly into the bodily fluids of the brain. Certain semiconductor elements are known to be pressure-sensitive, and therefore semiconductor elements may be positioned on the interventional device at the tip and/or at multiple locations on the lateral surface of the interventional device and be electrically connected to an outside source to interpret the signals.

At least one method according to the present invention for sensing the intracranial pressure within a patient comprises inserting the above described apparatus into the brain of a patient, visualizing the tissue around the apparatus and visualizing the apparatus itself by magnetic resonance imaging particularly in effect by continuous or real time visualization with MRI or fluoroscopy, less preferred), and positioning the apparatus within the device under magnetic resonance imaging, and reading signals from said pressure sensing element to indicate hydrostatic pressure or changes in hydrostatic pressure within the brain during or shortly after delivery of chemical agents into the fluids and/or tissue of the brain. Upon reading changes in hydrostatic pressure of the brain that exceeds a predetermined amount, an indication of the exceeding of that predetermined amount may be provided to an operator of the apparatus, as by an alarm, special image on a video screen, or by an automatic function change directed by memory (computer) associated with the system. For example, the apparatus may also comprise at least one lumen for delivery of chemicals to the patient, and chemicals are delivered to the patient through the at least one lumen, and upon reading changes in hydrostatic pressure of the brain that exceeds a predetermined amount during delivery of chemicals to the patient from the lumen, an indication of the exceeding of that predetermined amount is provided to an operator of the apparatus. This can be effected upon the indication of the exceeding of that predetermined amount by an artificial memory, that artificial memory then signaling the apparatus to reduce the amount of chemical being delivered to the patient.

One aspect of this invention is to provide a device and method for acute measurement of ICP in the human central nervous system during magnetic resonance (MR) imaging procedures, particularly those involving direct injection or perfusion of drugs into the brain parenchyma, with the measurement and sensing being performed during those stages of the drug delivery where pressure changes may occur.

A second aspect of this invention is to provide a device and method for controlling the delivery of drug solution in response to detected alterations in ICP during magnetic resonance (MR) imaging procedures, particularly those involving direct injection of drugs into the brain parenchyma. This can be particularltly accomplished by the use of at least two pressure sensing elements, one distal and one proximal to the point of insertion of the interventional device. By having separated pressure sensing devices, a pressure gradient may be measured and/or the direction of flow and variations in flow from the point of introduction can be determined.

A third aspect of this invention is to provide a device as an alternative method for the detection and measurement of intracranial pressure, replacing devices and methods such as conventional ventriculostomy with an external transducer, an epidural strain gauge transducer, a pressure sensitive epidural capsule, a pressure sensitive subdural capsule, or a subarachnoid pressure transducer.

A fourth aspect of this invention is to provide a device and method to record intracranial pressures over extended time periods such as hours or days in patients that have been subjected to compression or shift of the cerebral ventricles resulting from severe head injury, tumor, or other causes of acute or chronic intracranial hypertension.

A fifth aspect of the invention is to provide a device and method to accurately record ICP in the lateral ventricle, epidural, subdural, and subarachmoid spaces in patients in whom these fluid-filled cavities have been compressed by trauma or medical condition, including tumors or hematoma, or may have thick or mobile walls or small volumes that cannot be reliably penetrated with standard ventricular catheters when they are attempted to be positioned under stereotaxic guidance.

A sixth aspect of this invention is to provide a device and method for safely measuring ICP with minimal risk of infection caused by meningitis or ventriculitis, minimal risk of intracranial hemorrhage from opening the dura or puncturing the ventricle, and minimal interference to the patient.

A seventh aspect of this invention is to provide a device and method for MR image-guided therapeutic drainage of cerebrospinal fluid to relieve acute rises in ICP.

An eighth aspect of this invention is to provide a device and method for injection of a small volume of MR-visible gas for MR-ventriculography while monitoring ICP.

A ninth aspect of this invention is to provide a device and method for a hydrocephalus pressure valve and self-sealing port for regulating the flow of cerebrospinal fluid through the catheter after placement of the catheter tip into the ventricle, subarachnoid, subdural, or epidural space under MR imaging guidance.

A tenth aspect of the present invention is to provide a device substantially made of MR-visible elastomeric hydrogel, polymer, thermoplastic, or similar low friction material to minimize abrasive damage to the brain during insertion.

DETAILED DESCRIPTION OF THE INVENTION

Targeted drug delivery into the brain desires precise anatomically localized delivery of the drug to the desired tissue and benefits from the differentiation or localization of normal and abnormal tissues. Present systems of image-guided placement of intracranial probes, such as drug delivery catheters, include framed and frameless technologies, which typically use images acquired preoperatively to create a three-dimensional space on which the surgical navigation is based. Framed systems use externally applied frames to establish the fiducials for navigation, whereas frameless systems use optical, electromagnetic, or ultrasound sensors and mechanical arms to track the position of surgical tools and instruments during surgical procedures. U.S. patent application Ser. No. 08/857,043, filed May 15, 1997 in the names of J. Kucharczyk and R. Moseley describes a system and methodology where MRI techniques can be used to visualize the parenchymal delivery of materials in real time to a patient. This is a highly effective and useful system, and can even suggest delivery rates by contrast differences. However, significantly more data is crucial or even critical for the medical profession to have during intracranial drug delivery.

The use of MRI to provide intraoperative imaging guidance is a relatively new concept made feasible by the development of new MRI systems that provide high spatial and temporal resolution imaging in conjunction with multiplanar and volumetric three-dimensional data acquisition, thereby making possible interactive image plane definition to facilitate surgical localization and targeting of target artifacts such as a lesion and improving intraoperative navigation of devices and materials towards a target area. Intra-operative MR imaging enables the surgeon to non-invasively visualize tissue planes beyond the surface of the tissue under direct evaluation during a clinical procedure. Moreover, MR imaging enables differentiation of normal tissues from abnormal tissues, and the imaging can display critical structures such as blood vessels in three dimensions. Thus, high-speed MR-guided therapy offers an improved opportunity to maximize the benefits of minimally invasive procedures in real-time.

Pressure changes may occur both during delivery (from the introduction of volumes of drug into a relatively closed environment or an environment where incremental pressure build-up can occur) and after delivery. Pressure build-up after delivery can occur because of physical reactions with the environment of the drug delivered, chemical reactions of the delivered drug with the environment, and biological responses (including allergenic or anaphylactic responses) to the delivered drug. A relatively closed environment where pressure could build-up would be a region where the rate of drug delivery administration is greater than the possible rate of natural removal of the liquid from that region within the patient.

MR imagers which permit continuous real-time visualization of tissues during surgical and endovascular procedures have already been developed. U.S. Pat. Nos. 5,410,287, 5,519,372, 5,565,831 and 5,713,357 provide illustrative examples of such systems. Newer generations of MR scanners provide frequently updated images of the anatomical structures of interest, providing a nearly real-time image for the medical practitioner. This close to real-time imaging capability makes it possible to use high-speed MR imaging to observe the effects of specific interventional procedures, such as endovascular catheter tracking and intracranial administration of drug agents to targeted tissues, as disclosed by U.S. patent applications Ser. Nos. 08/857,043, 08/856,894, 08/916,596, 09/131,031, and 09/174,189, co-authored by at least some of the present inventors, which U.S. Applications are incorporated herein by reference for their disclosure or materials, methods, devices and systems.

Drug delivery devices, such as catheters, that are MR-visible can be monitored by MR imaging, thus making intra-operative verification of catheter location possible during MR-guided procedures. U.S. patent application Ser. No. 08/857,043 describes a method for MRI image-guided drug delivery. U.S. patent application Ser. Nos. 08/856,894, and 08/916,596 disclose active MR visualization of catheters and other interventional probes by means of radiofrequency microcoils positioned on the device, such as along the distal axis of the device. U.S. patent application Ser. 09/131,031, discloses a method and medical device for neurological interventions using nonlinear magnetic stereotaxis combined with MR imaging in order to perform image-guided targeted drug delivery in the brain. Alternative means of using MR signals to localize and track devices with small coils that are placed within the body are taught by U.S. Pat. Nos. 5,211,165, 5,307,808, 5,318,025 and 5,715,822. The relevant disclosure of these patents as they relates to the subject of the present invention are also incorporated herein by reference.

The present invention discloses a device and method for monitoring (intracranial pressure) ICP during MR image-guided neurosurgical procedures, such as intracranial drug delivery procedures, wherein an MR-compatible microsensor pressure sensitive device or, for example, amicrosensor pressure sensitive transducer coupled to a pressure sensing diaphragm located at either or both the tip and/or lateral surfaces of an MR-compatible drug delivery catheter or multi-lumen drug delivery catheter detects and monitors local and regional changes in ICP, particularly during and after delivery of liquid drug agents. The invention also provides a method for negative feedback control of drug delivery in response to elevations of brain tissue pressure so as to minimize increases in ICP related to intracranial drug delivery or other medical procedures (e.g., stimulation of natural production or release of compounds by the body). It is important to remember that the cells of the brain are very sensitive to damage from pressure and that the effects of even locally increased pressure can have severe effects upon the patient. At the same time, it is necessary to deliver or infuse or retroperfuse an adequate amount of drug at an adequate rate at the proper location. The ability to locally determine the pressure changes effected by drug delivery adds another, literally critical parameter to the diagnostic tools and controls available to the surgeon and medical technicians. Previously, even with the enhanced ability to view the actual location of drug delivery, even on a molecular level, there was not any mechanism for also considering and determining local pressure effects, which cannot presently be measured by non-invasive technology (such as X-ray, fluoroscopy, or MRI). The present invention provides not only a mechanism and device for measuring local intracranial pressure, but doing so with real time MRI guidance contemporaneously with drug delivery.

In a non-limiting example of a method of the invention, a variable-length concentric MR-visible multi-lumen catheter is provided, as by forming it with extrusion of a tubular assembly with both porous and non-porous tubular components made of MR-visible elastomeric hydrogel, polymer (thermoplastic, or crosslinked) or similar low friction material intended to minimize abrasive damage to the brain during insertion. The catheter and especially the distal tip of a multi-lumen catheter assembly is positioned using MR imaging at the target intraparenchymal tissue, or in a lateral cerebral ventricle, cerebral cistern, subarachnoid space, subdural or extradural spaces, or venous sinus.

A general description of the practice of the present invention comprises a method for measuring or monitoring the intracranial pressure in a human or non-human body, comprising:

obtaining a magnetic resonance image of a body part to establish a target (region or tissue) location in need of therapy;

inserting the interventional medical device into the body; directing the interventional device to the appropriate area by any convenient means, including manual pressure, mechanical means, robotic control and the like; moving the interventional device within the body to the specific location in the body, changing the magnetic field with the electromagnet or otherwise providing a current or field to generate a responsive RF field;

superimposing or contemporaneously displaying (in real time, for example) on the magnetic resonance image of said target tissue a display of the location of the interventional device (or medical probe) in relation to said target tissue;

treating the target, for example, by delivery of drug to an area near the target; and using the fluid pressure sensing device to determine local fluid pressure, particularly while the target is under MR viewing (e.g., real time or essentially continuous viewing).

The pressure sensing device delivers the signal to an external monitoring or viewing or analytical system as described in greater detail herein so that the pressure can be monitored.

In certain mechanically directed systems, such mechanical means may include, for example, magnetic stereotaxis. This type of alternative system within the practice of the present invention may be employed, for example, as by magnetically coupling a magnetic object to a device and the using a magnetic field of an electromagnet to position the coupled device. This alternative form of process within the concept of mechanical or robotic movement may continue with disengaging the magnetic object from the device or probe by altering the connector. The device may then be directed back out of the body, either removing or leaving the magnetic object.

In a narrow aspect of the invention, the medical probe may comprise, for example, an MR-visible catheter, and the preferred method comprises positioning the medical probe occurs within the vasculature, ventricles, or tissue of the brain and the magnetic resonance image is of diagnostic quality. Typical preferred processes include an MR-visible drug delivery device used to treat a brain disorder, such as a tumor, venous disfunction, organ dysfunction, tissue damage, chemical deficiency, or other chemically treatable condition by acute, subacute or chronic infusion of at least one material.

An apparatus for the determination or monitoring of intracranial pressure in one aspect of the invention may comprise an article that is insertable into the tissue or vasculature of the brain, the article comprising a pressure sensing element, a signal transmitting connector connecting the pressure sensing element and a signal reader (as herein defined), the signal reader being able to read signals from the pressure sensing element to indicate hydrostatic pressure or changes in hydrostatic pressure. A preferred pressure sensing element comprises a solid state pressure sensing element, such as a device that comprises a diaphragm, with the diaphragm having one surface that is exposed to an environment in which the pressure sensing elements is placed. A typical design of this device, particularly with a physical diaphragm, would have a second surface of the diaphragm defining part of an internal cavity within the pressure sensing element, and movement of the diaphragm causes changes in pressure within the internal cavity. The pressure reading functional element of the device (e.g., an electronic pressure-sensing element) may be present within the internal cavity and the pressure sensing element is preferably attached to the connector or any externally transmitting system (even potentially RF) by electrical attachment of the pressure reading device to the connector or transmitting system.

Another way of describing a method of the invention for sensing the intracranial pressure within a patient comprises inserting the apparatus described herein into the brain of a patient, visualizing the tissue around the apparatus and the apparatus itself by magnetic resonance imaging, and positioning the apparatus within the device under magnetic resonance imaging, and reading signals from said pressure sensing element to indicate hydrostatic pressure or changes in hydrostatic pressure within the brain. The method may include a step wherein upon reading changes in hydrostatic pressure of the brain that exceeds a predetermined amount, an indication of the exceeding of that predetermined amount is provided to an operator of the apparatus. The apparatus also may comprise at least one lumen for delivery of chemicals to the patient, and chemicals are delivered to the patient through the at least one lumen, and upon reading changes in hydrostatic pressure of the brain that exceeds a predetermined amount during delivery of chemicals to the patient from said lumen, an indication of the exceeding of that predetermined amount is provided to an operator of the apparatus. The method may provide the indication of the exceeding of that predetermined amount by an artificial memory, that artificial memory then signals the apparatus or the operator to reduce the amount of chemical being delivered to the patient.

In a method of the invention, the implantable MR-visible multi-lumen catheter includes, in one or more tubing conduits, a pressure-sensing element, such as a solid-state microchip pressure-sensing device, DNA structure electrobiological sensing device, liquid crystal pressure-sensitive device, physio-electrochemical pressure sensitive sensing device, bacterial-electrogenerating pressure sensing device, any system that has electrical current passing through it and whose resistivity, conductivity and/or electrical flow change with pressure, electropolymer (polymers that alter their conductivity or generate charge flow under pressure) pressure-sensing device and the like enclosed inside an MR-compatible materials such as nitinol, titanium, polymeric composition or other MR-compatible material casing, said ICP device preferably comprising a pressure-sensitive component, such as a diaphragm (although direct fluid access to the device, with the device electrically or radiofrequency connected to an external receiving system is also functional) at the tip of a fiber optic catheter, whereby the displacement of the diaphragm is proportional to the change in the ICP. The degree of displacement of the diaphragm or a change in pressure within a cavity within the device is sensed and indicates not only a change in pressure, but also the amount of change in pressure and indicates the absolute pressure in contact with the diaphragm. The signals produced by the locally inserted device are transmitted to a reading or analytical system such as a direct view (monitor, CRT) system or a computer. Information may be initially and/or subsequently stored for further analysis or review, but the preferred method of practice involves the signals being converted by hardware (circuit board or computer) or software into a set of imageable signals, so that they can be readily or essentially instantaneously viewed during the procedure. The 'viewing' may be performed by the doctor, clinician or technical assistant, or can be read by the computer with respect to the pressure signal. That is, either a separate visual image identifying pressure levels or gradients (either by a color differentiated or optical density differentiated image) or a direct alphanumeric indication of the local pressure may be provided for view or for mechanical (e.g., computer) analysis and signaling. The computer may provide various levels of indication (visual or audio) that certain pressures are present, how the pressure is varying (e.g., increasing, decreasing, cyclic changes, or remaining steady) and/or the image viewed by the doctor, clinician, technician may provide a warning on the viewing screen within the image (e.g., color change, pulsing of the image, etc.) or in a separate area of view outside of the area of clinical observation (e.g., in a remote corner of the screen). The computer may be of any commercial variety having sufficient memory and speed to enable analysis of the pressure data. The same computer used for the real-time MRI visualization may be used, or a second computer used specifically for the pressure monitoring functions of the present invention.

In at least one but not every method of the invention, an implantable MR-visible multi-lumen catheter includes, in another tubing conduit, a hydrocephalus pressure valve and self-sealing port made of MR-compatible material (as generally and specifically described elsewhere herein). This may be used in some instances, for example, for regulating the flow of cerebrospinal fluid through the catheter after placement of the catheter tip into the ventricle, subarachnoid, subdural, or epidural space under MR imaging guidance. Such MR-compatible cerebrospinal fluid valves have been described previously in the medical literature, for example, in *Neurosurgery,* 1997, Volume 40, pages 1050–1057. When used in combination with the ICP measuring systems, apparatus and methods of the present invention, the safety and conditions of the patient are better monitored and safeguarded.

Figures 1, 2:
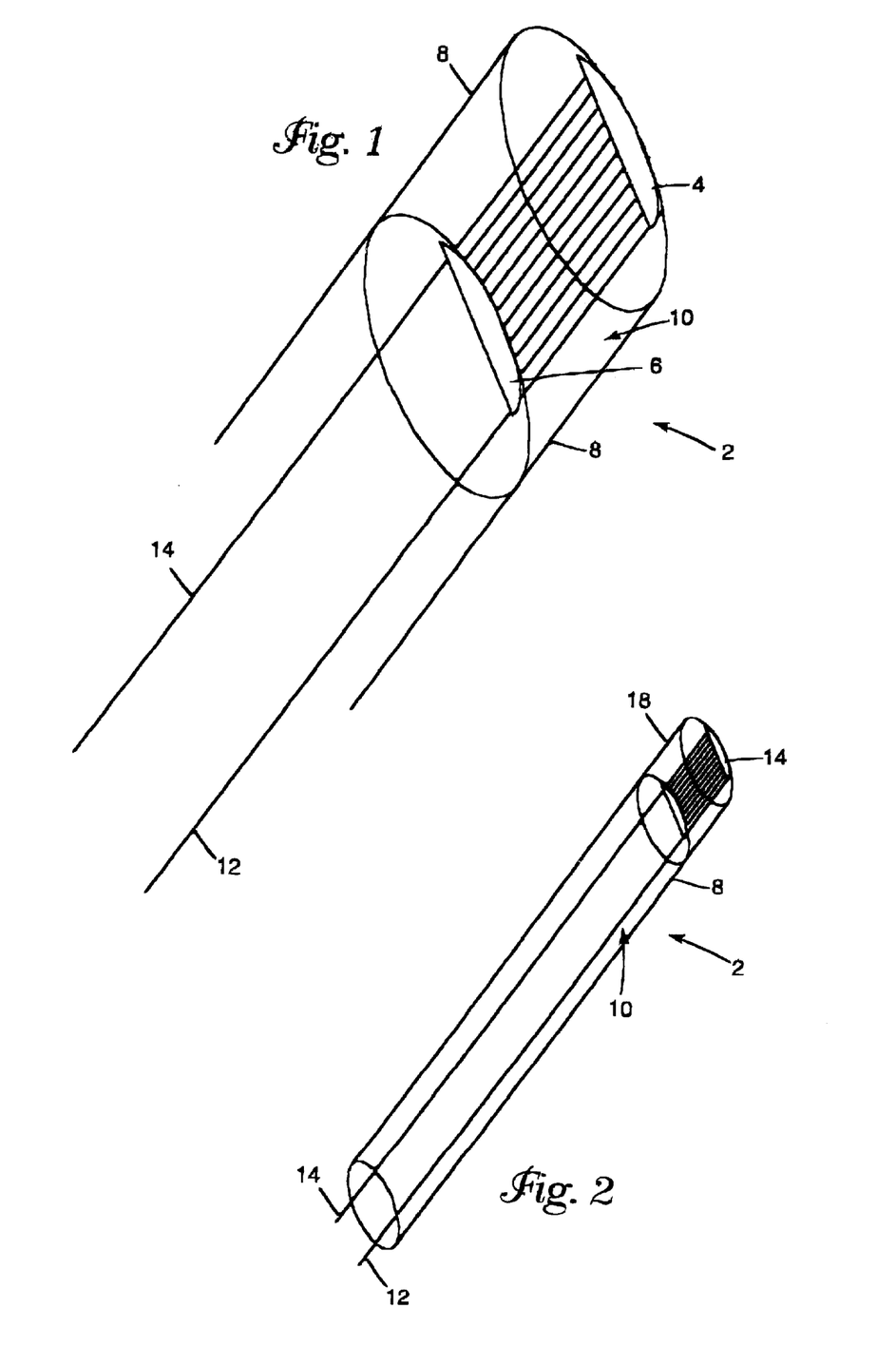
FIG. 1 is a schematic of a generic catheter having two pressure-sensing devices according to the practice of the present invention.
FIG. 2 shows a sectional view of a microsensor pressure transducer coupled to a pressure sensing diaphragm located at the distal terminus and the lateral aspect of the MR-compatible catheter shown in FIG. 1.

FIG. 1 is a schematic of a generic catheter 2 having two pressure-sensing devices 4 and 6 according to the practice of the present invention. The catheter wall 8 has the a pressure-sensing device of connected segments 4 and 6 (here shown as pressure sensing diaphragm) on a lateral surface 10 of the catheter. Electrical connections 12 and 14 connect the segments of the pressure sensing devices 4 and 6 to an outside or external reader or recorder (not shown). The catheter is shown without the ue of a series of microcoils to enhance the field external to the cather, but such microcoils, as disclosed in the art such as U.S. Pat. No. 5,964,705, may be used to improve some aspects of visualization and thereby treatment performance. Thus, the pressure-sensing devices according to the present invention may be used with or without microcoils to enhance MR field response.

FIG. 2 shows a sectional view of a catheter in which a microsensor pressure transducer (not shown) can be coupled to a pair of pressure sensing diaphragms 14 located at the distal terminus 18 and the lateral aspect 10 of the MR-compatible catheter 2 shown in FIG. 1. The transducer (not shown) or additional devices, subcomponents or elements may be provided within the catheter, locating these additional devices within the cavities between the microcatheters, internal walls, connectors and the like.

Figure 3:
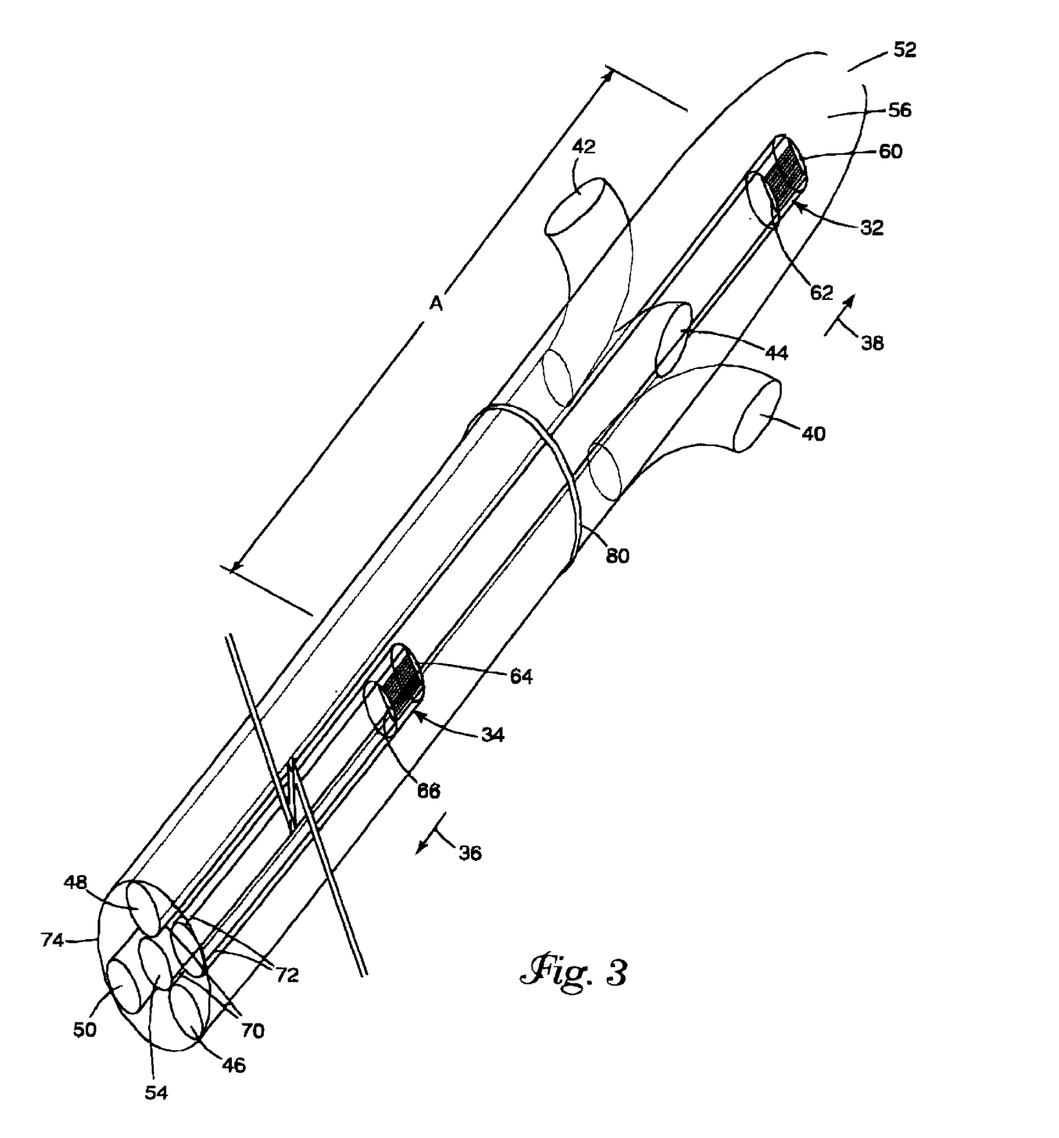
FIG. 3 shows a multilumen drug deliver device having sets of pressure sensing elements at a distal and a proximal end of the multilimen catheter.

FIG. 3 shows a multilumen drug deliver device 30 having sets of pressure sensing elements 32 and 34 at a distal 38 and a proximal 36 end of the multilumen catheter 30. Three subcatheters or microcatheters or lumens with external ports 40, 42 and 44 are shown. The entrance to the lumens with external ports 40, 42 and 44 are also respectively shown as 46, 48 and 50. An exit port 52 and inlet port 54 for another tip exitting lumen 56 is also shown. It is to be noted that the lumens with external ports 40, 42 and 44 are located between the two pressure sensing gauges 32 and 34 so that when materials exits from the lumens with external ports 40, 42 and 44, pressure may be sensed in either a distal 38 direction or proximal 36 direction from the point of introduction of the delivered material (not shown). The separation between the sets of pressure sensing elements 32 and 34 at a distal 38 and a proximal 36 end of the multilumen catheter 30 enable different pressure to be measured between the separation distance A between the sets of pressure sensing elements 32 and 34 at a distal 38 and a proximal 36 end of the multilumen catheter 30. By separately receiving and/or reading the different signals from the sets of pressure sensing elements 32 and 34 at a distal 38 and a proximal 36 end of the multilmen catheter 30, a gradient (with two determinant points) may be measured. With more pressure sensing elements (not shown), a more defined gradient can be measured. Information is electrically transmitted through the sets of electrical connectors 70 and 72 at the proximal end 74 of the multilumen catheter 30.

In one practice of the invention, a patient may undergo a high-resolution MR scan of the brain to anatomically localize in 3D the location of the target tissues (not shown) requiring image-guided treatment. The resulting high-resolution 3D MR image is automatically segmented to produce enhanced visualization of the anatomy of the target lesion and the surrounding tissues. The imaging data is also provided in registry to the patient's anatomy so that trajectories for advancing and placing the medical probe placement can be defined, and so that the position of the device within the patient can be depicted on displayed images. The pressure sensing elements may be individually identified on the MR visualization (because of their own MR response) or estimated with respect to the position of an MR marker (e.g., 80 in FIG. 3).

A fundamental requirement for MR monitoring of therapeutic interventions is usually implementation of an MR pulse sequence with appropriate spatial and temporal resolution. For monitoring purposes, several MR sequences are known in the art that have adequate temporal resolution to be useful with the present invention. Preferred are pulse sequences such as fast spin echo pulse sequences, various gradient echo pulse sequences, and echo-planar pulse sequences, which produce reasonably high-resolution images with a short (<1 second) acquisition time. One example of a preferred pulse sequence is the recursive formulation of the correlation method, as described by Cox et al. (*Magn Reson Med,* 1995; 33:230–236), wherein multiple linear regressions of the voxel time series is performed against known reference waveforms, thereby producing up-to-date MR images within 1 second of data acquisition. In the MR imaging method described by Cox et al., data are acquired at 106 16-bit samples/sec for all pulse sequences, and are digitally filtered and subsampled to the desired bandwidth before reconstruction. The amount of CPU time spent is proportional to the number of raw data points, such that a 64×64 image matrix typically takes 80–100 msec and a 128×128 image matrix typically takes 200–400 msec. The widespread availability of high speed, high precision A/D (analog to digital) converters and low inductance local gradient coils makes it possible to perform real-time imaging and reconstruct an entire region of anatomy, such as the brain, in a few seconds. With rapid and significant advances in artifical intellegence technology, these particular descriptions are clearly merely exemplary, with any functional data flow, pulse sequence, time periods, and capacities that can perform the generic tasks being suitable for practice of the present invention.

The catheter assembly preferably has an inner diameter of at least 4 French (about 1.35 mm), and may be any size capable of interventional use, such as 5, 7, 8, 10 French (e.g., 4–12 French or 5–10 French, or 7–9 French internal diameters for the microcatheters) or the like. An outer diameter of about 2–5 or 2–4 mm, may generally be comfortably used for the catheter, and an overall catheter length of 10–25 cm or greater may be used with the catheters, with the dimensions of the microcatheters being designed to fit within the internal cavity or lumen of the catheter. The MR-visible ICP device preferably contains a passive resonant circuit consisting of a coil and a capacitor. Pressure is transmitted to the bioacceptable core placed on the bellows, and the movement of the (bioacceptable core changes the resonant frequency. Absolute pressure is measured by a sensor, with a preferred pressure range of ±25 mmHg to ±75 mmHg, a preferred accuracy of +/−1.5% full scale (F.S.), preferred temperature error of +/−0.2%/degree, preferred linearity of +/−0.5% F.S. (between 0 and +75 mmHg) and 1.0% F.S. (between ±25 and 0 mmHg), preferred repeatability of 0.5% F.S., preferred hysteresis of 0.3% F.S., preferred sensitivity of 0.2 mmHg, preferred limit of atmospheric pressure (sensor) 964~1072 millibar, preferred limit of atmospheric pressure (meter) 85–1180 mb, and preferred sampling frequency of 50 times/sec. These preferences should not be limiting, with one skilled in the art identifying where variations are acceptable for economic reasons and within medically acceptable or tolerable practices.

The MR-visible ICP device e.g., 30 is used for therapeutic drainage of cerebrospinal fluid to relieve acute rises in ICP during and after drug delivery into the brain parenchyma. In order to maintain ICP within a normal physiologic range, a normally closed valve opens in response to increased ICP. The valve incorporates an injectable reservoir dome, an occluder for selective flushing, and non-metallic MR-compatible materials, such as polypropylene, polyamide, fluorinated polymer, polyurethane and silicone elastomer. The reservoir is designed to allow multiple punctures with a 25-gauge (0.51 mm)or smaller needle. Integral connectors facilitate attachment of the catheter.

As previously mentioned, among the mechanical or robotic navigation techniques useful for the MR-visible drug delivery probe disclosed by the present invention can be navigation by magnetic stereotaxis (MSS) to the target tissue and/or advanced into the patient via endovascular, intracerebroventricular, or intraparenchymal entry ports based on real-time or near real-time MRI data, such as disclosed in U.S. patent application Ser. No. 09/131,031 co-authored by one of the present co-inventors. In one embodiment of the present invention, a plurality of medical probes, each with an MSS-responsive magnetic tip disposed at the distal end, are sequentially guided by MSS to targeted locations in the cerebral vasculature, ventricles or parenchyma. As each probe is positioned at the appropriate MRI-determined target location, its MSS-responsive magnetic tip is retracted, thereby rendering the probe insensitive to MSS during placement of the next probe. These medical probes preferably have a linearly arranged array of radiopaque and MR-visible markers disposed at the distal end to provide easily identifiable reference points for trackability and localization under MR imaging and X-ray fluoroscopy guidance. Additionally, active MR visualization of the medical probe is achieved or enhanced by means of RF microcoils disposed along the distal axis of the probe, as disclosed by U.S. patent applications Ser. Nos. 08/856,894 and 08/916,596, coauthored by the present inventors and commonly assigned U.S. Pat. No. 5,984,705. MR visibility can thereby be variably adjusted based on requirements related to the degree of signal intensity change for probe localization and positioning, enhancement along the shaft of the probe, enhancement around the body of the probe, visibility of the proximal and distal ends of the probe, degree of increased background noise associated with probe movement, and other factors which either increase or suppress noise and artifacts associated with the probe.

In another embodiment of the invention, the ICP monitoring device is inserted into a lateral cerebral ventricle, cerebral cistern, subarachnoid space, subdural or extradural spaces, or venous sinuses, under MR imaging guidance, and is used to record intracranial pressures over hours to days in patients undergoing diagnostic or therapeutic neurologic interventions.

In a preferred embodiment of the invention, the MR-visible ICP device is used under direct MR imaging guidance to accurately catheterize the lateral ventricle, epidural, subdural, and subarachnoid spaces in patients in whom these fluid-filled cavities have been compressed by tumor or hematoma, or may have thick or mobile walls or small volumes that cannot be reliably penetrated with standard ventricular catheters positioned under stereotaxic guidance.

In another preferred embodiment, the MR-visible intracranial pressure device is safely positioned under MR imaging guidance to measure ICP with minimal risk of infection caused by meningitis or ventriculitis, minimal risk of intracranial hemorrhage from opening the dura or puncturing the ventricle, and minimal interference to the patient.

In the preceding detailed description of the preferred embodiments, references made to the accompanying drawings which form a part hereof, and in which is shown by way of illustration specific preferred embodiments in which the invention may be practiced. These embodiments are described in sufficient detail to enable those skilled in the art to practice the invention, and it is to be understood that other embodiments may be utilized and that structural, logical, physical, architectural, and electrical changes may be made without departing from the spirit and scope of the present invention. The preceding detailed description is, therefore, not to be taken in a limiting sense, and the scope of the present invention is defined only by the appended claims and their equivalents.

What is claimed is:

1. An apparatus for the determination or monitoring of intracranial pressure comprising an interventional device that is insertable into a tissue or vasculature of the brain, said interventional device comprising at least two pressure sensing elements located on lateral surfaces of said interventional device, a signal transmitting connector connecting said at least two pressure sensing elements and a signal reader, the signal reader being able to read signals from said at least two pressure sensing elements to indicate hydrostatic pressure or changes in hydrostatic pressure, wherein one of said at least two pressure sensing elements is located closer towards a tip of the interventional device than at least one other another of said at least two pressure sensing elements, and wherein there is at least one drug delivery lumen located between two pressure sensing elements of said at least two pressure sensing elements.

2. The apparatus of claim 1 wherein said at least two pressure sensing elements comprise a solid state pressure sensing element.

3. A method for sensing the intracranial pressure within a patient comprising inserting the interventional device of the apparatus of claim 1 into the brain of a patient, visualizing the tissue around the apparatus and the apparatus itself by magnetic resonance imaging, and positioning the apparatus within the device under magnetic resonance imaging, and reading signals from said pressure sensing element to indicate hydrostatic pressure or changes in hydrostatic pressure within the brain.

* * * * *